United States Patent [19]
Boyle, III

[11] Patent Number: 6,156,959
[45] Date of Patent: *Dec. 5, 2000

[54] CACTACEAE PLANT AND PROGENY

[75] Inventor: Thomas H. Boyle, III, Amherst, Mass.

[73] Assignee: Universtiy of Massachusetts, Boston, Mass.

[ * ] Notice: This patent is subject to a terminal disclaimer.

[21] Appl. No.: 09/062,825

[22] Filed: Apr. 20, 1998

[51] Int. Cl.$^7$ .............................. A01H 5/10; A01H 5/00; A01H 5/02; A01H 1/04

[52] U.S. Cl. ........................... 800/323; 800/298; 800/260

[58] Field of Search ............................. Plt./372; 800/298, 800/323, 260

[56] References Cited

PUBLICATIONS

Boyle et al., *J. Amer. Soc. Hort. Sci.*, 119(5):1060–1067, 1994.
Barthlott et al., *Bradleya*, 13:43–79, 1995.

*Primary Examiner*—Lynette R. F. Smith
*Assistant Examiner*—Melissa L. Kimball
*Attorney, Agent, or Firm*—Fish & Richardson, P.C., P.A.

[57] ABSTRACT

A new and distinct plant variety of the Cactaceae family arising as a spontaneous mutation of *Hatiora x graeseri* 'Evita', is distinguishable from its progenitor by larger flowers, larger pollen grains, larger and thicker phylloclades, reduced branching, and a flower longevity of about 8 days. The new variety, termed 'Avalon', is a stable periclinal cytochimera with a diploid epidermis and tetraploid subepidermis. Seeds produced by 'Avalon' plants ('Avalon' S1 seeds) can be germinated to yield plants that have the same morphological characteristics as 'Avalon' itself. Moreover, sexually and asexually reproduced progeny of 'Avalon' S1 seeds also resemble 'Avalon.'

9 Claims, No Drawings

CACTACEAE PLANT AND PROGENY

FIELD OF THE INVENTION

The invention relates to a new and distinct plant variety of the Cactaceae family and progeny thereof.

BACKGROUND OF THE INVENTION

Several species of the Cactaceae family are commercially grown as flowering potted plants, including asexually-propagated varieties of the genus Hatiora [=*H. gaertneri, H. rosea,* and their interspecific hybrids (=*H. x graeseri*)]. The genus Hatiora is commonly known as Easter cactus. Varieties of Easter cactus flower mainly in March, April, and May in the northern hemisphere. Flowering plants typically are marketed from late winter until late spring.

SUMMARY OF THE INVENTION

New Easter cactus plants are disclosed herein. The new plants include plants designated as Avalon S1, which are obtained as the selfed progeny of a self-fertile variety designated *Hatiora x graeseri* 'Avalon.' 'Avalon' possesses large cyclamen-purple flowers that are distinguishable from known related varieties and that have acceptable flower longevity for marketing purposes. 'Avalon' S1 plants also possess these same characteristics.

Morphological characteristics of 'Avalon' S1 include a degree of branching of about 2–3, flowers that are about 5.7 to about 7.7 cm in diameter, a cyclamen-purple flower color of RHS 74 B/C and a flower longevity of about 8 days. Progeny of Avalon S1 possess these same characteristics.

'Avalon' S1 can be used to make new Easter cactus plants by providing a phylloclade segment of 'Avalon' S1 or its progeny and growing the segment to obtain a new Easter cactus plant. Alternatively, a new Easter cactus plant can be made by providing a seed of 'Avalon' S1 or its progeny and growing the seed into the new Easter cactus plant.

Other features and advantages of the invention will be apparent from the following description of the preferred embodiments thereof, and from the claims. Abbreviations and nomenclature, where employed, are deemed standard in the field as commonly used in professional publications such as those cited herein. All patents and publications referred to herein are expressly incorporated by reference in their entirety.

DETAILED DESCRIPTION OF THE PREFERRED EMBODIMENTS

The 'Avalon' variety is a stable cytochimera, having a diploid epidermis (L1 layer) and a tetraploid subepidermis (L2 layer). The tetraploid chromosome number is 2n=44. This cytochimera has remained stable through at least eight cycles of vegetative propagation; no revertants to the diploid state have been observed.

The 'Avalon' variety was isolated from the variety 'Evita' and exhibits many improved characteristics over 'Evita.' 'Avalon' phylloclades are longer, wider, and thicker than those of 'Evita.' 'Avalon' plants are more erect and stiffer and are less prone to stem breakage than 'Evita' plants. 'Avalon' plants exhibit less branching compared to 'Evita', with comparisons made on either pruned or unpruned plants.

On unpruned plants, 'Avalon' typically produces about two to three new phylloclades per segment, e.g., an average of about 1.8 to less than about 2.8 new phylloclades per segment, e.g., about 2.0 to less than about 2.8 new phylloclades per segment, or about 2.2 to about 2.6 phylloclades per segment. 'Evita' produces about three to four new phylloclades per segment. The degree of branching typically is determined by counting the number of tertiary segments and secondary segments produced on an unpruned primary segment, and calculating the ratio of tertiary segments per secondary segment.

Flowers on 'Avalon' plants are considerably larger than those on 'Evita' plants. 'Avalon' flowers have a diameter of about 5.7 to about 7.7 cm, e.g., about 6.0 to about 7.0 cm, determined by averaging the tip-to-tip distance at 2 or 3 places across a flower at midday. The maximum petal width for 'Avalon' flowers is about 8.0 to about 10.5 mm, e.g., about 8.0 to about 10.0 mm or about 8.0 to about 9.0 mm. However, 'Avalon' and 'Evita' are essentially identical in flower color and phylloclade color, as described herein.

'Avalon' flowers remain open about 6 to about 11 days, or about 7 to about 9 days, which is about 3 to 4 days less than 'Evita' flowers. The dry weight of 'Avalon' flowers is about 80 to about 160 mg, e.g., about 100 to about 150 mg. Pollen diameter at dehiscence is larger for 'Avalon' than for 'Evita,' averaging about $81.5 \pm 8.5$ μm for 'Avalon and about $59.6 \pm 3.7$ μm for 'Evita.'

'Avalon' phylloclade segments are larger and thicker than those of 'Evita,' having a dry weight from about 0.15 mg to about 0.28 mg per segment, e.g., from about 0.18 mg to about 0.25 mg per segment. 'Avalon' segments have an area of about 8.2 to about 14.8 $cm^2$, e.g., about 8.6 to about 12.6 $cm^2$. 'Avalon' segments have a succulence of from about 18.0 to about 22.0 μg/$cm^2$, e.g., about 18.5 to about 20.5 μg/$cm^2$, measured as segment fresh weight per unit area.

'Avalon' is unusual among Hatiora varieties in that it is self-fertile, i.e., self-pollination by either natural or artificial methods results in viable seed being produced on 'Avalon' plants, i.e., 'Avalon' S1 seed. Progeny of 'Avalon' derived by self-pollination possess substantially all the morphological characteristics of 'Avalon' itself. In particular, selfed progeny of 'Avalon' possess longer and wider phylloclades, less branching, and larger flowers that remain open for a somewhat shorter period of time compared to 'Evita.' The diameter of pollen produced by 'Avalon' S1 plants is similar to the diameter of pollen produced by 'Avalon' plants.

'Avalon' S1 is obtained by growing 'Avalon' plants in a greenhouse and allowing natural self-pollination to occur at sexual maturity. Self-pollination of 'Avalon' can also be carried out manually by techniques known in the art. See, e.g., Boyle, T. H., Menalled, F. D., and O'Leary, M. C., "Occurrence and physiological breakdown of self-incompatibility of Easter cactus," *Journal of the American Society for Horticultural Science,* 119(5):1060–1067 (1994). If desired, 'Avalon' plants can be grown in isolation to minimize the presence of stray pollen from cactus plants other than 'Avalon.'

S1, S2, etc. progeny of 'Avalon' possess the distinguishing morphological characteristics of 'Avalon' itself, and, in fact, cannot be readily distinguished from 'Avalon' itself except by microscopic examination. Under these conditions, selfed progeny plants can be distinguished from 'Avalon' by larger stomatal openings and by a lower stomatal density for selfed progeny. In addition, guard cells of selfed progeny are somewhat larger than guard cells of 'Avalon' plants. These microscopic characteristics do not affect the appearance and desirable morphological characteristics of the flowers and phylloclades of 'Avalon' S1.

The selfed progeny of 'Avalon' can be utilized in a number of different ways. The morphological similarity between selfed progeny and 'Avalon' permits such progeny to be marketed in a manner similar to 'Avalon.' That is, sexually reproduced progeny can be used to obtain stem cuttings for further propagation by asexual methods. In addition, selfed progeny plants can be grown to sexual maturity and used in breeding programs to introduce desirable features of 'Avalon' into other varieties and to create new, novel Easter cactus varieties.

It is apparent from the above that the term progeny includes descendants of a particular plant or plant line, e.g., seeds developed on a plant as well as plants derived from such seeds. Progeny of a plant include seeds formed on $S_1$, $S_2$, $S_3$, and subsequent generation plants, seeds formed on $F_1$, $F_2$, $F_3$, and subsequent generation plants, or seeds formed on $BC_1$, $BC_2$, $BC_3$, and subsequent generation plants. Thus, selfed progeny of 'Avalon' includes not only the S1 progeny of the initial self-pollination, but also S2, S3, and subsequent generations.

As discussed herein, progeny also refers to descendants obtained by asexual propagation. Asexual propagation is carried out by using a plant cutting suitable for regenerating a whole plant, e.g., having roots, phylloclade segments and, at sexual maturity, flowers. Cuttings used for asexual propagation of Easter cactus are phylloclade segment ("stem") cuttings, typically about 5 to about 7 centimeters in length, taken from a plant that is about 6 months to about 48 months of age. Such cuttings are rooted and grown to regenerate a whole plant by techniques known in the art.

Seeds of 'Avalon' S1 have been deposited with the American Type Culture Collection depository, Manassas, Va., under the terms of the Budapest Treaty, affording permanence of the deposit and ready accessibility thereto by the public if a patent is granted. The seeds are taken from the same deposit maintained by the inventor since prior to the filing date of this application. All restrictions on accessibility will be irrevocably removed upon the issuance of a patent; seeds will be maintained with all the care necessary to keep them viable and uncontaminated for a period of 30 years, or 5 years after the most recent request, or for the effective life of the patent, whichever is longer, and will be replaced if they become non-viable during that period. Ready accessibility, however, is not to be construed as a license to practice the invention.

| Line | Accession No. | Deposit Date |
| --- | --- | --- |
| 'Avalon' S1 | 209770 | April 14, 1998 |

The following examples are provided for illustrative purposes and are not intended to limit the scope of the invention as claimed herein. Any variations in the exemplified compositions and methods which occur to the skilled artisan are intended to fall within the scope of the present invention.

EXAMPLES

Example 1

Morphological Description of 'Avalon'

This example and the following examples use many techniques well-known and accessible to those skilled in the arts of plant biology, the manipulation of plant tissue and the culture and propagation of plants. This Example describes the identification and isolation of 'Avalon' from the Easter cactus variety 'Evita.'

Hatiora 'Evita' is a diploid Easter cactus variety with a chromosome number of 2n=22. Flowers of 'Evita' are about 5.6 cm in diameter with perianth-segments (undifferentiated sepals and petals) that are up to 6.7 mm in width and 33 mm in length. Perianth-segments of 'Evita' are predominantly cyclamen purple, having a color as determined by the Royal Horticultural Society (RHS) Colour Chart of RHS 74 B/C (Royal Horticultural Society, London, in association with the Flower Council of Holland, Leiden). Flower longevity for 'Evita' is about 11 to 12 days. 'Evita' is male and female fertile but highly self-incompatible, so that fruit set is rarely attained when flowers are self-pollinated.

A mutated branch was observed on an 'Evita' plant growing in a greenhouse at Amherst, Mass. Stem cuttings were taken from the mutated branch and were rooted at the same greenhouse. Through successive cycles of asexual propagation, it was established that plants asexually propagated from the mutated branch were clearly distinguishable from 'Evita' plants or any other Hatiora variety plants known to the inventor. Asexually propagated plants derived from the mutated branch appeared uniform and stable, i.e., all relevant characteristics remain unchanged through asexual reproduction. Asexually propagated plants derived from the mutated branch were designated as the variety 'Avalon.'

A detailed morphological characterization of 'Avalon', including the color(s) of each plant part, is presented below. Color was characterized qualitatively using the Royal Horticultural Society (RHS) Colour Chart. Fully expanded flowers and phylloclades were compared with the RHS Colour Chart to determine color chip(s) closest to the respective color. Color names were obtained from the Table of Cross References that is supplied with the RHS Colour Chart. The plants described herein were grown using standard horticultural practices and were less than 20 months old from the time of initial propagation to the time at which measurements were made. Plants were grown at Amherst, Mass., in shaded greenhouses (≈2,000 footcandles light intensity) with a temperature regime of 60° F. nights/70–80° F. days. Plants were fertilized at each watering with 225 ppm nitrogen (N) using a 15% N - 16% $P_2O_5$ - 17% $K_2O$ fertilizer. Flower longevity was measured by growing plants in a growth chamber at a constant temperature of 20° C.

I. Name: *Hatiora x graeseri* 'Avalon'.

II. Parentage: Spontaneous mutation of *Hatiora x graeseri*, known commercially as 'Evita'. 'Evita' has phylloclades that are narrower in width and shorter in length than 'Avalon'. In addition, 'Evita' has smaller flowers with narrower and shorter perianth-segments. In addition, 'Evita' exhibits greater branching and has longer-lasting flowers than 'Avalon'.

III. Classification:
  A. Botanic.-(reference: W. Barthlott and N. P. Taylor. 1995. Notes towards a monograph of Rhipsalideae (Cactaceae). *Bradleva* 13:43–79). (1) Family: Cactaceae. (2) Tribe: Rhipsalideae. (3) Genus: Hatiora Britton & Rose (formerly Rhipsalidopsis). (4) Subgenus: Rhipsalidopsis (Britton & Rose) Barthlott. (5) Species: *x graeseri* Barthlott ex D. Hunt [=interspecific hybrids of *H. gaertneri* (Regel) Barthlott and *H. rosea* (Lagerheim) Barthlott].
  B. Commercial.-Easter cactus.

IV. Form: A shade-loving, succulent tropical perennial that exhibits a strictly determinate growth pattern and produces a series of leafless, elliptic-oblong stem segments (phylloclades) with crenate margins. Plants in natural settings are either epiphytic or lithophytic.

V. Stems:

A. General. Stems are comprised of a series of leafless, elliptic-oblong segments (phylloclades) with crenate margins and (usually) an oblique base. Phylloclades are usually flatted but may occasionally be angular with 3 to 4 ribs. Axillary buds (areoles) restricted to margins and apices of phylloclades. At the apex, areoles are crowded together to form a "composite" areole, whereas areoles that develop below the apex are solitary. New phylloclades and flowers developing almost exclusively from composite areoles. Phylloclades are capable of forming adventitious roots.

B. Phylloclades.- (1) General: Succulent, elliptic-oblong, determinate, and (usually) flat with a composite areole at the apex, 4- to 5-crenate along the margins with an areole in each notch, and an oblique base. Areoles produce setaceous spines from 0.5 to 10 mm in length. (2) Midrib: (a) General - Extends longitudinally from base to apex and comprised of a cylinder of pith surrounded by branching network of vascular tissue. Prominent only in dried specimens. (b) Texture - Succulent, glabrous to slightly coriaceous with a waxy epidermis when recently mature, and becoming corky and woody with age. (c) Size (at maturity) - 1. Length: Usually between 50 and 70 mm and averaging about 60 mm. 2. Thickness: Usually between 3 and 5 mm at the midrib and averaging about 4 mm. (d) Color (at maturity) - Usually moderate olive green (RHS 137 B/C). (3) Margins: (a) General - 4- to 5-crenate from base to apex and moderately tapered from midrib to margins. (b) Texture - succulent, with a glabrous to slightly coriaceous epidermis when recently mature, and becoming corky and woody with age. (c) Size (at maturity) - 1. Thickness: About 1–2 mm in the area adjacent to the margin. 2. Width: Usually between 14 and 16 mm as measured from the midrib to the most offset marginal areole and averaging about 15 mm. Usually 10 to 13 mm distance between adjacent marginal areoles and averaging about 12 mm. 3. Color (at maturity): Beetroot purple (RHS 71A). The pigmented area averages 2- to 3-mm in width and forms a continuous band around the margin of the phylloclade. (4) Teeth: none. (5) Areoles: (a) Composite (apical) areole - Usually 6 to 14 mm in length (averaging about 10 mm) and 1 to 2 mm in width, producing setaceous spines from 0.5 to 10 mm in length. New phylloclades and flowers develop almost exclusively from composite areoles. (b) Axillary (lateral) areoles - Usually 0.5 to 1.0 mm in diameter with setaceous spines from 0.5 to 3 mm in length.

Table 1 compares the segment morphology and degree of branching for 'Evita' and 'Avalon' Easter cactus. The data show that 'Avalon' tertiary segments have a larger area than those of 'Evita.' 'Avalon' also exhibits a lower degree of branching than does 'Evita.'

TABLE 1

Segment Morphology and Degree of Branching for 'Avalon' and 'Evita' Easter Cactus

| Clone | Tertiary segments | | | Degree of Branching (Tertiary segments/ Secondary segment) |
|---|---|---|---|---|
| | dry wt. (mg) | Area (cm$^2$) | Succulence ($\mu$g/cm$^2$) | |
| Evita | 0.15 | 8.2 | 17.7 | 2.8 |
| 'Avalon' | 0.21 | 10.6 | 19.5 | 2.4 |
| Significance[a] | *** | *** | ** | ** |

[a], *: Significant difference by F test at $P \leq 0.01$ or $P \leq 0.001$, respectively. Data collected after 48 weeks of growth under greenhouse conditions. Data collected on 10 plants (pots) per clone.

VI. Flowers:

A. General.- Sessile, actinomorphic, perfect, epigynous, and developing predominately on the composite areoles of apical phylloclades. Perianth-segments 20 to 25, margins entire, the outermost perianth-segments subulate, the innermost perianth-segments linear-lanceolate and slender-acute. Perianth-tube short. Stamens numerous, inserted in one series at the base of the perianth. Stigma lobes 6 to 8 and usually 7. Ovary obconic, naked, and 4- to 7-angled (usually 5). Flowers nyctinastic and odorless.

B. Perianth-segments.-(1) General: about 20 to 25, inserted on top of ovary, margins entire. The outermost perianth-segments subulate. The innermost perianth-segments linear-lanceolate and slender-acute. Perianth-segments scarcely united at the base, more or less spreading. Color at anthesis - Cyclamen/purple (RHS 74 B/C).

C. Androecium (stamens).-(l) General: Inserted in one close series at the base of the perianth, inclined towards the center of the flower, anthers producing viable pollen. (2) Stamen number: About 185 to 200. (3) Filaments: (a) General - Short, capillary, terete, and glabrous. (b) Shape - Short, capillary, terete. (c) Texture - Glabrous. (d) Color (at anthesis) - Cyclamen purple (RHS 74A). (e) Size (fully expanded flower) - 1. Length: Between 8 and 14 mm and usually 12 mm. 2. Diameter: Usually about 0.2 mm at insertion and tapering to about 0.1 mm at distal end. (4) Anthers: (a) General - Four longitudinally dehiscent pollen sacs arising from a connective by which they are attached to the filament. (b) Shape - Oblong. (c) Texture - Waxy. (d) Color (at maturity) - Aureolin (RHS 12A). (e) Size (at dehiscence) - 1. Length: Usually 0.8 to 1.0 mm. 2. Diameter: Usually 0.5 to 0.7 mm. (f) Pollen grains (at dehiscence) - 1. Diameter: 81.5±8.5 $\mu$m. 2. Percent viable pollen (estimated with fluoroscein diacetate): 85 to 95%.

D. Gynoecium (pistil).- (1) General: Pistil with compound, parietal placentation. Style slender, elongate. Stigma lobes 6–7, erect at anthesis and reflexed when mature, linear, white, papillate. (2) Style: (a) General - Slender and inserted at ovary. (b) Shape - Elongated, slender, terete. (c) Texture - Glabrous and waxy. (d) Color - White (RHS 155D) at proximal end and gradually becoming fuchsia purple (RHS 67B) at distal end. (e) Size (at anthesis) - 1. Length: Usually 15 to 23 mm. 2. Diameter: Usually 0.8 to 0.9 mm halfway between the proximal and distal ends. (3) Stigma: (a) General - Stigma lobes 6–7, linear, erect at anthesis but gradually becoming reflexed with age. (b) Shape - Linear with rounded apices, upper surface and sides covered with elongate papillae. (c) Texture - Fleshy. (d) Color - White (RHS 155D). (e) Size - 1. Length: About 3 to 5 mm. 2. Diameter: About 0.8 mm. (4) Ovary: (a) General - Inferior, devoid of areoles, occasionally with 1 or more subulate scales, (usually) 6–7 carpels with numerous ovules. (b) Shape - Obovoid, truncate-umbiculate at the distal end, sharply 5- to 6-angled. (c) Texture - Glabrous and waxy. (d) Color - Moderate olive green (RHS 137 B/C) at base and beetroot purple (RHS 71A) along edges of ribs at the distal end. (e) Size - 1. Length: About 9 to 11 mm. 2. Diameter (maximum): About 8 to 10 mm.

Table 2 compares flower morphology and longevity for 'Evita' and 'Avalon'. The data show that 'Avalon' flowers are significantly larger than 'Evita' flowers and that 'Avalon' flower longevity is significantly less than that of Evita.

TABLE 2

Flower Morphology and Longevity for 'Evita' and 'Avalon' Easter Cactus

| Clone | Flower Diameter (cm) | Flower Dry Weight (mg) | Maximum Petal Width (mm) | Flower Longevity (days) |
| --- | --- | --- | --- | --- |
| 'Evita' | 5.6 | 77.7 | 7.9 | 11.5 |
| 'Avalon' | 6.7 | 125.1 | 9.3 | 8.3 |
| Significance[a] | *** | *** | *** | * |

*, ***[a]: Significant difference by F test at $P \leq 0.05$ and $P \leq 0.001$, respectively. Data collected on 10 flowers per clone (flower morphology) or 20 flowers per clone (longevity).

Example 2

Selfed Progeny of 'Avalon'

This Example describes the production of 'Avalon' S1 plants. About three 'Avalon' plants from Example 1 were isolated from other plants by placing them in a pollination cage. The plants were then allowed to self-pollinate. There were about 10–15 fruits per plant and an average of about 200 seeds per fruit. Mature seeds (S1 generation) were then germinated by imbibing seeds in $H_2O$ and incubating on moist filter paper at 20° C., 12 hours light/12 hours dark for 30 days in an incubator. The germination tests revealed that about 20% of the seeds were viable.

S1 plants were grown in the greenhouse at 20–25° C., 12/12 hours light/dark, in 10 cm pots containing a soilless mix composed of peat, perlite and vermiculite.

S1 plants typically were visually indistinguishable from 'Avalon'. S1 plants grew and flowered in about the same amount of time as 'Avalon' plants. Flower color for 'Avalon' and 'Avalon' S1 flowers was exactly the same. Flowers on S1 plants had an average flower diameter of about 6.8 cm and an average flower longevity of about 8 days. The range of values for flower diameter and flower longevity of S1 plants were clearly distinct from the corresponding values for 'Evita', i.e., there was no overlap in flower diameter or flower longevity values between S1 plants and 'Evita' plants. Similarly, the degree of phylloclade branching and segment morphology averages for S1 plants were indistinguishable from 'Avalon,' and none of the S1 plants had a degree of branching or segment morphology that overlapped the range of values observed for 'Evita.' The average pollen grain diameter on 18 'Avalon' S1 plants ranged from 85.4 $\mu$m to 94.2 $\mu$m. The overall average was about 81.5 $\mu$m (microns).

Examination of various plant parts under the microscope at 160× magnification showed that guard cells were approximately 1.2× longer for S1 plants compared to 'Avalon' plants. The guard cells of S1 plants were about 28 to 32 $\mu$m in length, compared to about 25 $\mu$m in length for 'Avalon'. The stomatal density of S1 plants was about 9 to 12 per $mm^2$, whereas the stomatal density of 'Avalon' was about 22 per $mm^2$.

After about 6 months of growth in the greenhouse, phylloclade tissue was removed from representative S1 plants. Subepidermal layers from the phylloclades were examined for chromosome number. The analysis showed that S1 plants retained the tetraploid chromosome constitution of the 'Avalon' subepidermal layer.

Example 3

Asexual Propagation of S1 Plants

This Example describes vegetative propagation of S1 plants. S1 progeny plants were vegetatively propagated by using stem cuttings from 12 month-old plants. Stem sections about 2.5 cm in width and about 6 cm in length were removed and rooted in a soilless medium containing peat, perlite and vermiculite. Plantlets were transferred to pots after about 50 days and grown in a greenhouse as described in Example 2. The resulting progeny plants retained all visually observable morphological characteristics of the parent S1 plants after 8 cycles of vegetative propagation. In addition, such progeny retained the tetraploid chromosome number of the parent S1 plants. Morphological characteristics of the asexually propagated progeny that were retained included flower color, flower size, and flower longevity.

While various embodiments of the present invention have been described in detail, it is apparent that modifications, extensions, adaptations and optimizations may occur to those skilled in the art. It is to be expressly understood that such modifications and adaptations and so on are within the spirit and scope of the present invention, as set forth in the claims.

What is claimed is:

1. An Easter cactus seed designated 'Avalon' S1 and represented by seed deposited as ATCC Accession Number 209770.

2. A plant produced by the seed of claim 1.

3. A flower produced by the plant of claim 2.

4. A plant cutting of the plant of claim 2.

5. Progeny of the plant of claim 2, said progeny having a degree of phylloclade branching of about 1.8 to about 2.8, a flower diameter of about 5.7 to about 7.7 cm and a flower color of RHS 74 B/C.

6. The progeny of claim 5, wherein said progeny are obtained by asexual propagation.

7. The progeny of claim 5, wherein said progeny are obtained by sexual reproduction.

8. A method of making an Easter cactus plant, comprising the step of growing a phylloclade segment of an Easter cactus plant designated 'Avalon' S1, represented by seed deposited as ATCC Accession Number 209770, or progeny into said Easter cactus plant.

9. A method of making an Easter cactus plant, comprising the step of growing a seed of an Easter cactus plant designated 'Avalon' S1, represented by seed deposited as ATCC Accession Number 209770, or progeny thereof into said Easter cactus plant.

\* \* \* \* \*